United States Patent
Bernabei

(10) Patent No.: US 6,409,736 B1
(45) Date of Patent: *Jun. 25, 2002

(54) DERMABRASION APPARATUS OPERATING BY A FLOW OF REDUCING SUBSTANCES, HAVING DISPOSABLE STERILIZED COMPONENTS

(75) Inventor: Gian Franco Bernabei, Florence (IT)

(73) Assignee: Mattioli Engineering Ltd., London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/562,005

(22) Filed: May 2, 2000

Related U.S. Application Data

(63) Continuation of application No. 08/797,909, filed on Feb. 10, 1997, now Pat. No. 6,120,512.

(30) Foreign Application Priority Data

May 10, 1996 (IT) .......................................... FI96A0108

(51) Int. Cl.$^7$ ............................................... A61B 17/50
(52) U.S. Cl. ..................................... 606/131; 604/289
(58) Field of Search ......................... 606/131; 604/289, 604/290, 310

(56) References Cited

U.S. PATENT DOCUMENTS

| 3,608,553 A | | 9/1971 | Balamuth ................... 606/131 |
| 6,039,745 A | * | 3/2000 | Di Fiore et al. ............ 606/131 |

FOREIGN PATENT DOCUMENTS

| IT | 67279A/85 | * 10/1987 |
| IT | F194A000131 | 2/1996 |

* cited by examiner

Primary Examiner—Michael H. Thaler
(74) Attorney, Agent, or Firm—Foley & Lardner

(57) ABSTRACT

A dermabrasion apparatus operates by a flow of a mixture of air and reducing substances. This mix is conveyed by a pneumatic system through a contacting handle. The apparatus includes a carrying tray that houses a vacuum pump and a cup. Inside the cup, there is placed a mixing bottle and a collecting bottle. The handle and the bottles are disposable sterilized components.

4 Claims, 2 Drawing Sheets

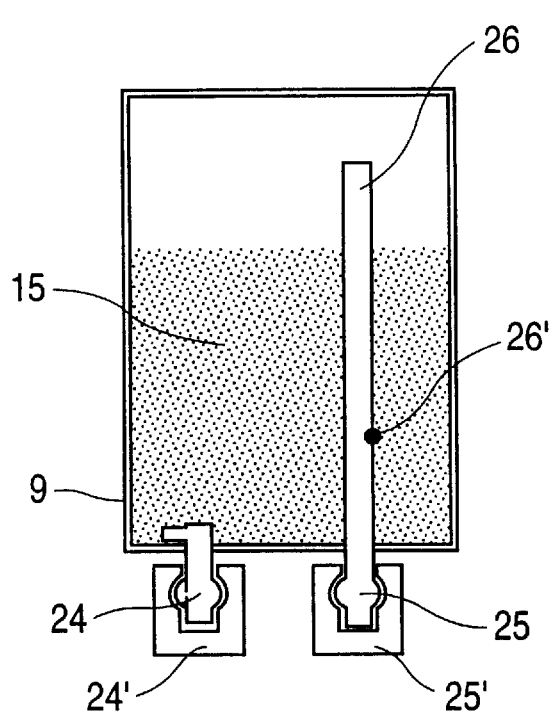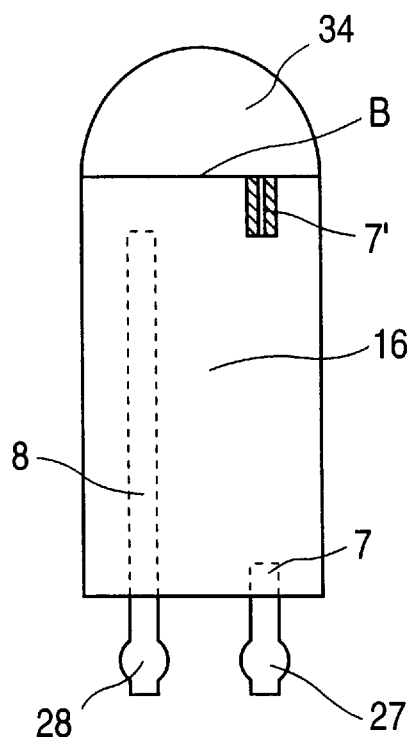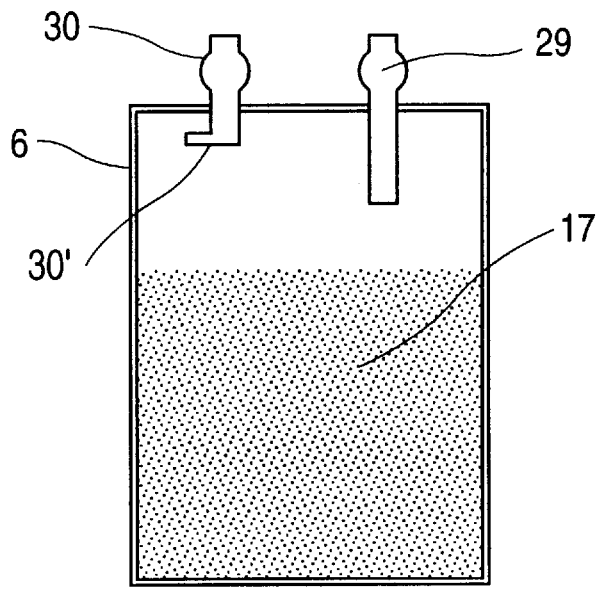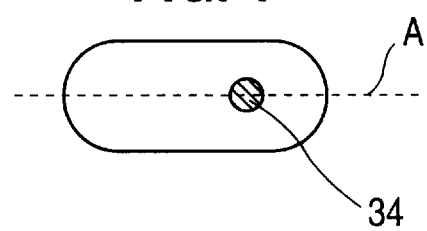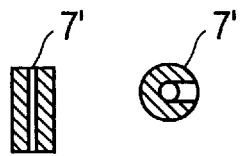

DERMABRASION APPARATUS OPERATING BY A FLOW OF REDUCING SUBSTANCES, HAVING DISPOSABLE STERILIZED COMPONENTS

This application is a continuation of application Ser. No. 08/797,909, filed Feb. 10, 1997, now U.S. Pat. No. 6,120,512.

FIELD OF THE INVENTION

The present invention relates to the field of the cosmetic and microsurgical treatments. In particular it refers to a microdermabrasion apparatus and to its most relevant components, operating by a pressurized flow of air and reducing substances, preferably corundum ($Al_2O_3$).

BACKGROUND OF THE INVENTION

Several technical solutions to produce a microdermabrasion apparatus are known, all comprising vacuum means and/or pressurizing means which send a flow of air and reducing substances on a tissue portion to be treated and then remove from that portion the abraded particles. Such solutions have a drawback in that the sterility of the various components is not guaranteed, unless by complicated and expensive procedures.

Italian patent application FI94A000131 describes a dermabrasion apparatus operating by a flow of reducing substances. The apparatus comprises a compressor, a vacuum pump, and three detachable onepiece components, a mixing bottle, a collecting bottle for the abraded particles and a contact handle to touch the tissue to be treated. Those parts are preferably made of glass or plastic material and can be easily sterilized.

However, such apparatus has some drawbacks due to the fact that the air pressurization is performed by a compressor placed inside the apparatus and therefore difficult to be sterilized. Thus, during the treatment, the compressor could be infected by bacteria which would be afterwards conveyed on the patient's skin by the pneumatic system. Furthermore, the above-mentioned one-piece components are sterilized after the apparatus has been used, but they do not guarantee a proper sterility when the apparatus performs succeeding treatments on different patients. A further drawback is that dangerous contaminations can occur when the mixing bottle is filled with new reducing substances or when the collecting bottle is cleaned of the abraded particles.

OBJECT OF THE INVENTION

A first object of the invention is to ensure the highest sterility of the apparatus components in whatever circumstances, also when sterilization means as UV ray or autoclave are not available. A further object of the invention is to obtain easy replaceable, low cost apparatus components.

SUMMARY OF THE INVENTION

The above objects have been reached according to the invention by a microdermabrasion apparatus provided with disposable sterilized components consisting of easily interchangeable one piece blocks. Such components comprehend an already filled mixing bottle containing the reducing substances, a collecting bottle for the abraded tissue particles, and a handle contacting the tissue during the treatment. All those components are manufactured and sealed in a sterilized environment. According to an embodiment of the invention, the components are made of plastic material, preferably polycarbonate, in order to lower the costs, and to make them particulary suitable for disposable use. According to a still further embodiment of the invention, after manufacturing, the components can be packed in sterilized packagings to form either a single component or a multi-component kit. Thus, all the possible contamination risks are avoided, from the manufacturing to the use of the components. In order to avoid the contamination of the reducing substances, preferably corundum, with particles of the handle material abraded in the use, the portion of the handle most subjected to the abrasion effect is an abrasion-proof block made of a suitable hard material, for example ceramics. According to a further embodiment of the invention, the source of pressurized air, or of an other suitable gas, is constituted by one disposable bottle of sterilized pressurized air. In such a way sterility is guaranteed to all the apparatus components exposed to contamination risks, for each single treatment. A further advantage is due to the low cost production of such components.

DRAWINGS

Still further advantages will be evident from the following description and from the annexed drawings given as a non limitative example, in which:

FIG. 1 schematically shows the layout of the apparatus according to the invention;

FIG. 4 shows a preferred embodiment according to the invention of the mixing bottle filled with reducing substances;

FIG. 5 shows a preferred embodiment of the collecting bottle according to the invention;

FIG. 6 shows a preferred embodiment of the contacting handle according to the invention;

FIG. 7 shows a top view of the handle of FIG. 6;

FIGS. 8a, 8b show different views of the abrasion-proof block of the handle of FIG. 6.

DETAILED DESCRIPTION OF THE INVENTION

Figure 1:
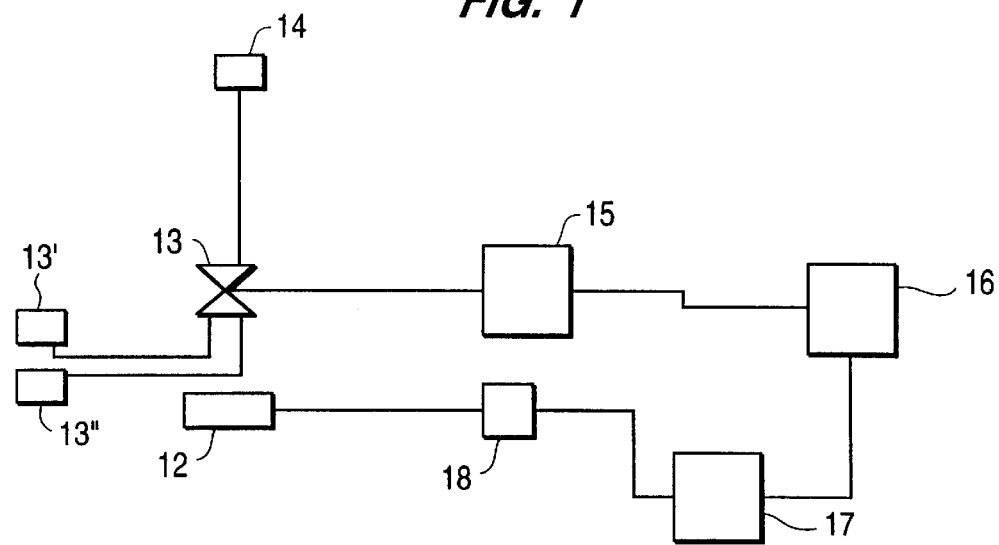
Figure 2:
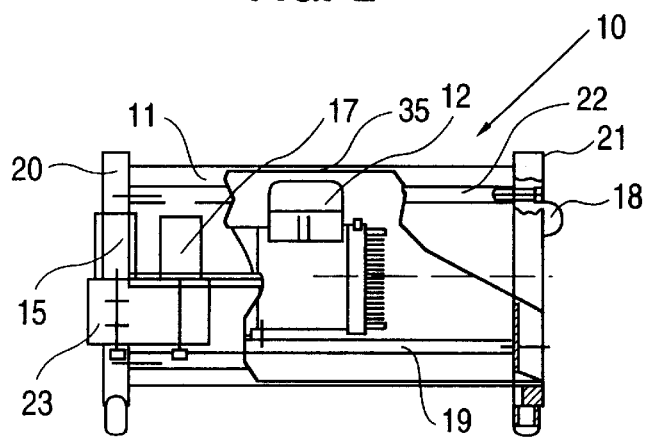
FIG. 2 shows a side view of the apparatus.
Figure 3:
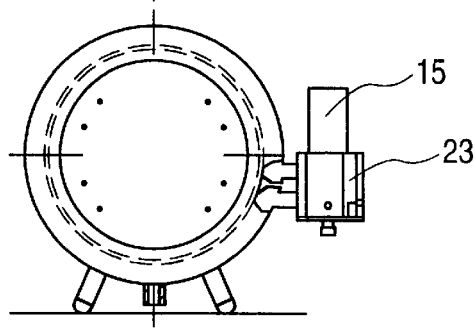
FIG. 3 shows a front view of the apparatus of FIG. 2.

Refering to FIGS. 1–3, a microdermabrasion apparatus 10 according to the invention comprises a carrying tray 11 housing: a vacuum pump 12, a mixing bottle 15 containing the reducing substances and a bottle 17 to collect the reducing substances and the abraded tissue particles after use. Apparatus 10 is connected by a pneumatic system to a handle 16 intended to contact the tissue portion during the treatment. In the described embodiment, there is also provided a valve 13 controlled by a switch 14, for example a treadle switch, able to switch the air inlet from two different sources 13', 13". The first source is a bottle of pressurized and sterilized air, and the second source is air at the environmental pressure. Downstream from the bottle 17 and upstream from the vacuum pump 12, there is also provided a filter 18 to stop possible small particles flowing accidentaly from the bottle 17.

In FIGS. 2, 3, there is illustrated a one possible configuration of the carry tray 11, constituted by a casing 35, preferably made of plexiglass, and a bar 19 supporting the vacuum pump 12, where a couple of lateral flanges 20, 21 are connected by thread tierod 22. Carry tray 11 also includes a cup 23, fixed to the flange 20, which houses the mixing bottle 15 and the collecting bottle 17. Flange 21 holds the filter 18 placed immediately upstream of the vacuum pump 12. Referring to FIG. 4 the mixing bottle 15 is a substantially cylindrical one-piece block obtained, for example, by ultrasound welding following a horizontal junction line 9. Mixing bottle 15 is provided with connection pipes 24, 25 connected respectively with valve 13, not shown in the drawings, and with the pneumatic duct leading to the handle 16 according to the scheme of FIG. 1. Pipe connection 25 extends into mixing bottle 15 with a suction tube 26 having a hole 26' near the bottom wall of the mixing bottle 15, through which the reducing substances are introduced into the pneumatic system.

According to the invention, the mixing bottle 15 is filled with the corundum in an aseptic environment and thereafter is closed, preferably by welding, and then sealed by suitable plugs 24', 25'. For example, each plug 24', 25' can have a bottom rubber layer which is pierced by the extremities of corresponding connecting junctions of the cup 23 when the plugs are fitted into the cup 23. In such a way, the mixing bottle 15 is connected with the valve 13 and with the downstream handle 16.

Referring to FIG. 6, handle 16 is constituted by a substantially cylindrical one-piece block having an upper portion in cone shape of a hollow spherical cap. Handle 16 is provided with an inlet connection 27 corresponding to an inner tube 7 through which the air and the reducing substances enter into the spherical cap. After use, the reducing substances are removed from the spherical cap by a second tube 8 and a corresponding outlet connection 28. The handle spherical cap presents an opening 34, the rim of which defines the patient's tissue portion inpinged by the reducing substances ejected from the tube 7.

According to the invention, the upper end of tube 7, which is the part subjected to the highest abrasion, is provided with an insert block 7', shown in FIGS. 8a, 8b. Block 7' is a cylinder having an internal diameter smaller than the tube 7 diameter, so that in that point the flow area is smaller and the flow rate of the reducing substances increases. Block 7' is made of a hard material, preferably ceramics. In the described embodiment, handle 16 is constituted by two half parts symmetrical with respect to section A of FIG. 7 and manufactured by injection molding, together with the corresponding half parts of tubes 7, 8.

Before assembling, block 7' is inserted into the upper end portion of tube 7 and the spherical cap is put on so that, the opening 34 corresponds to the block 7' position. After that the assembly is closed, for example by ultrasound welding according to section A and section B between the spherical cap and the cylindrical body. Alternatively, the spherical cap is welded to the lower cylindrical body obtained by a single injection operation.

Referring to FIG. 5, it shows the collecting bottle 17, which is placed downstream of the handle 16 and upstream pump 12, according to the pneumatic system scheme of FIG. 1. collecting bottle 17 is constituted by a cylindrical hollow one-piece block provided with two upper connections 29, 30, the first operating as inlet of the reducing substances from handle 16, the second as passage of the air aspirated by the pump 12. Connection 30 is provided with an air filter 30' in order to avoid the passage of the used reducing substances and of tissue abraded particles towards the pump 12. In the described embodiment, collecting bottle 17 is assembled by welding according to section 6, the upper portion including connections 29, 30. Immediately downstream of the collecting bottle 17 is placed a filter 18 which is intended to filter possible small particles passed through the filter 30' collecting and conveyed towards the pump 12. Advantageously, the connections of collecting bottle 17 and handle 16 are provided with plugs similar to the already described plugs 24', 25' which are intended both to seal the collecting bottle 17 and handle 16 until they are first used, and to allow a quick connection to the pneumatic system. According to the invention, after manufacturing the mixing bottle 15, the collecting bottle 17 and handle 16 can be packaged, one by one or in a unique kit, in a sterilized packaging, possibly including the needed connection tubes. The one piece blocks constitute a kit of disposable components which allows ones to avoid the stages of filling with the reducing substances, cleaning of the abraded particles and of sterilization of the critical parts of the. apparatus, which stages until the present invention represented a drawback to treatment safety and a further increasing on costs and time. It is also possible to fix an expiring time for the sterility condition of the blocks contained in packaging kit according to the invention so that, according to such time, all the critical parts of the apparatus can be safety and quickly replaced due primarily to the described sealing plugs of blocks 15, 16, 17. The blocks 15, 16, 17 can be made of any suitable plastic or vetrous material. Anyhow, polycarbonate is preferred because it is a low cost material and is sterilizable by autoclave when a reuse of one or more components is needed. According to a further feature of the invention, the kit components present different colors in order to allow a better identification of their functions by the user.

What is claimed is:

1. Dermabrasion treatment kit, comprising:

a mixing bottle adapted to hold a dermabrasion substance therein, said mixing bottle having an input port and an output port;

a contacting handle configured to receive the dermabrasion substance from said mixing bottle and to provide the dermabrasion substance to a patient in contact with said contacting handle;

a collecting bottle configured to collect the dermabrasion substance from said contacting handle after the dermabrasion substance has made contact with the patient, said collecting bottle having an input port and an output port; and a tray for holding said mixing bottle and said collecting bottle in place, wherein input port and said output port of said mixing bottle and said input port and said output port of said collecting bottle are configured to be sealingly connected to said tray and to said contacting handle, via said tray, so as to provide the dermabrasion substance from said output port of said mixing bottle to said contacting handle via a first passageway within said tray, and so as to provide the dermabrasion substance from said contacting handle to said collecting bottle via a second passageway within said tray, so that said dermabrasion substance is sealingly protected from an exterior atmosphere as said dermabrasion substance travels from said mixing bottle to said contacting handle and then to said collecting bottle, wherein said mixing bottle and said collecting bottle are constructed from one of a plastic and a vetrous material.

2. Dermabrasion treatment kit according claim 1, wherein said mixing bottle present and said collecting bottle are constructed so as to have a different color with respect to each other in order to provide a better identification of said collecting bottle and said mixing bottle.

3. Dermabrasion treatment kit according to claim 1, wherein at least one of said mixing bottle, said contacting handle and said collecting bottle are packaged in a sterilized package prior to being assembled together to form said dermabrasion treatment kit.

4. Dermabrasion treatment kit according to claim 1, wherein at least one of said mixing bottle, said collecting bottle and said contacting handle is a plastic unit.

* * * * *